United States Patent
Rezkallah

(10) Patent No.: US 7,667,081 B2
(45) Date of Patent: Feb. 23, 2010

(54) METHOD FOR PURIFICATION OF GLYCEROL

(75) Inventor: Areski Rezkallah, Chauny (FR)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 12/004,547

(22) Filed: Dec. 21, 2007

(65) Prior Publication Data

US 2008/0249338 A1  Oct. 9, 2008

(30) Foreign Application Priority Data

Apr. 4, 2007  (FR) .................. 07 290412

(51) Int. Cl.
*C07C 29/74* (2006.01)
*C07C 29/76* (2006.01)

(52) U.S. Cl. .................................... 568/870

(58) Field of Classification Search ........ 568/870
See application file for complete search history.

(56) References Cited

U.S. PATENT DOCUMENTS 2,615,924 A  10/1952  Reents
4,990,695 A  2/1991  Buenemann et al.
7,126,032 B1  10/2006  Aiken

FOREIGN PATENT DOCUMENTS

GB  633343  12/1949
JP  58144333  8/1983

OTHER PUBLICATIONS

Aldrich Catalog, 1992-1993.*
Asher, et al., "Glycerol Purification By Ion Exclusion", J. Phys. Chem., vol. 60, pp. 518-521 (1956).
I. Miesiac, "Methods for Utilization of the Glycerine Fraction, a Rapeseed Oil Methanolysis By-Product", Przemysl Chemiczny, vol. 82, pp. 1045-1047 (2003).
Busby. G. W et al: "The purification of glycerol by Ion exchange" J. American Oil Chemists Society, vol. 29, pp. 316-320 (1952).
Product Information Sheet for Lewatit MDS 1368, 1993.
Dedardel, et al., "Ion Exchangers", Rohm and Haas Separation Technologies, vol. A 14, pp. 393-405, (1989).
Dorfner, et al., "Ion Exchangers", de Gruyter, p. 314, (1990).
Product Information Sheet for Lewatit MDS 1368 Na 350, 1991.

* cited by examiner

*Primary Examiner*—Elvis O Price
(74) *Attorney, Agent, or Firm*—Kenneth Crimaldi

(57) ABSTRACT

A method for purification of glycerol, especially crude glycerol from biodiesel production. The method uses gel-type acidic ion exchange resin beads to separate fatty acid salts and inorganic salts from the crude glycerol.

13 Claims, No Drawings

METHOD FOR PURIFICATION OF GLYCEROL

BACKGROUND

This patent application claims the benefit of the earlier filed European Patent application serial number 07290412.1 filed on Apr. 4, 2007 under 37 CFR 1.55(a).

This invention relates generally to a method for purification of glycerol, especially crude glycerol derived from biodiesel production.

High fuel prices and environmental concerns are driving development of alternative fuels, especially those derived from renewable resources. One such fuel, commonly known as "biodiesel" fuel, commonly contains methyl esters of fatty acids, and is burned in diesel engines. One source of biodiesel fuel is transesterification of triglycerides, such as vegetable oils with alcohols, typically with methanol. Glycerol is produced as a byproduct of this process, and typically is contaminated with salts of fatty acids and inorganic salts. The prior art discloses methods purification of glycerol, e.g., by ion exclusion chromatography in D. R. Asher & D. W. Simpson, *J. Phys. Chem.*, vol. 60, pp. 518-21 (1956).

However, poor separation is achieved by prior art methods.

The problem addressed by this invention is to find an improved method for purification of glycerol.

STATEMENT OF INVENTION

The present invention is directed to a method for purification of glycerol. The method comprises steps of (a) providing catalyst beads comprising gel-type acidic ion exchange resin, said beads having: (i) a uniformity coefficient no greater than 1.15; (ii) 4 wt % to 8 wt % monomer units derived from cross linker; and (iii) a harmonic mean particle size from 200 µm to 400 µm; and (b) allowing crude glycerol from biodiesel production to pass through of bed of said beads.

DETAILED DESCRIPTION

All percentages are weight percentages ("wt %"), and all temperatures are in ° C., unless otherwise indicated. Weight percentages related to ion exchange resins are based on dry resin. Fatty acids are acyclic aliphatic carboxylic acids containing from 8 to 22 carbon atoms; most commonly, they contain from 12 to 18 carbon atoms. With respect to carbon-carbon bonds, the fatty acids may be saturated, monounsaturated or polyunsaturated (typically 2 or 3 carbon-carbon double bonds).

In addition to glycerol, crude glycerol from biodiesel production typically comprises methanol, water, inorganic salts and salts of fatty acids. Salts usually are sodium and/or potassium salts. Levels of fatty acid salts typically are from 5% to 50%. Levels of inorganic salts are from 1% to 5%. These levels typically are expressed together in terms of total cation concentration, which usually is from 0.2% to 5%. In some embodiments of the invention, the total cation concentration is at least 0.5%, alternatively at least 1%. In some embodiments, the total cation concentration is no more than 4%, alternatively no more than 3%. Crude glycerol contains water, and may also be diluted further with water to reduce load on the column and aid in the separation, so that typical water levels can be from 5% to 40%. In some embodiments of the invention, glycerol concentration in the crude glycerol introduced into the resin bed is at least 20%, alternatively at least 30%, alternatively at least 40%, alternatively at least 50%, alternatively at least 60%, alternatively at least 70%, alternatively at least 75%. The method of this invention also can be used to purify crude glycerol obtained from other sources, including soap manufacture.

In some embodiments of the invention, the purification of glycerol is performed in a temperature range from 25° C. to 80° C. In some embodiments of the invention, the temperature is no greater than 70° C., alternatively no greater than 65° C., alternatively no greater than 60° C. In some embodiments of the invention, the temperature is at least 40° C., alternatively at least 45° C. Higher temperatures generally improve separation, but the present invention provides improved separation even at lower temperatures and higher glycerol concentrations than those typically used.

Typical flow rates for separation of glycerol according to this invention are from 0.2 to 1 bed volume ("BV")/hour. In some embodiments of the invention, the flow rate is at least 0.3 BV/hour, alternatively at least 0.4 BV/hour. In some embodiments of the invention, the flow rate is no more than 0.9 BV/hour, alternatively no more than 0.8 BV/hour.

The ion exchange resin used in the present invention is a gel-type resin, not a macroreticular resin. A macroreticular resin is a resin having a surface area from 25 $m^2/g$ to 200 $m^2/g$ and an average pore diameter from 50 Å to 500 Å; alternatively a surface area from 30 $m^2/g$ to 80 $m^2/g$ and an average pore diameter from 100 Å to 300 Å. Gel-type resins typically contain monomer units derived from cross linkers in amounts no greater than 10%. Suitable gel-type resins include, e.g., acrylic resins, styrenic resins, and combinations thereof. Resins contain polymerized units of a multiethylenically unsaturated monomer (cross linker). In some embodiments of the invention, the level of monomer units derived from cross linker in the resin is no more than 7.5%, alternatively no more than 7%, alternatively no more than 6.5%, alternatively no more than 6%. In some embodiments, the level of cross linker is at least 4.5%. In some embodiments, the average particle size of the gel resin is from 250 µm to 400 µm, alternatively from 250 µm to 350 µm. In some embodiments of the invention, the ion exchange resin comprises polymerized units of styrene and a crosslinker, e.g., divinyl aromatics; di-, tri- and tetra-(meth)acrylates or (meth)acrylamides; di-, tri- and tetra-allyl ethers and esters; polyallyl and polyvinyl ethers of glycols and polyols. In some embodiments of the invention, the crosslinker is diethylenically unsaturated, e.g., divinylbenzene (DVB). In some embodiments of the invention, the acid functionality of the ion exchange resin comprises sulfonic acid groups, carboxylic acid groups, phosphoric acid groups or a mixture thereof. A typical acidic ion exchange resin has from 0.4 to 8 meq/kg acid functionality, on a dry basis, alternatively at least 2 meq/kg, alternatively at least 4 meq/kg. Preferably, the acid functionality is in the form of sulfonic acid groups. The cation associated with the resin is not believed to be critical, but usually is sodium or potassium, depending on the predominant cation in the crude glycerol.

The uniformity coefficient of an ion exchange resin bead particle size distribution is a measure of the width of the size distribution curve. The uniformity coefficient is defined as d60/d10 where d60 is the size of the opening through which exactly 60% of the distribution passes, and d10 is the size of the opening through which exactly 10% of the distribution passes. In some embodiments of the invention, the uniformity coefficient of the resin beads is no greater than 1.10.

In the method of this invention, salts and colored impurities typically elute from the column earlier than the glycerol, which is obtained with much lower metal ion content and greatly reduced color.

The method of this invention may be performed using simulated moving bed technology or sequenced simulated moving bed technology to enable automated continuous purification of glycerol.

EXAMPLE 1

The jacketed chromatographic column (1.5 cm i.d×2 m) was heated up to 60° C. The temperature was maintained by circulating water through the jacket from a thermostatic bath. The chromatographic column was filled to a height of 194.6 cm (345 mL) with the potassium form of acidic cation exchange resin beads made from a sulfonated styrene/DVB copolymer, and having a harmonic mean size of 300 μm, cross linking level of 5% and uniformity coefficient no greater than 1.15. The resin bed was settled, and the resin bed temperature was allowed to equilibrate before the run. The feed solutions were prepared from pure glycerol solution and potassium chloride, and had a glycerol concentration of 68%, a potassium level of 4.2% and a pH between 5 and 9. A measured amount of feed solution was layered on the flooded resin bed and allowed to pass through the resin bed at a controlled flow rate (3 mL/min) by adjusting the rotation velocity of a peristaltic pump. Deionized water was used as elution solvent. The effluent was continuously analyzed by a differential refractometer detector. A conductimetric detector was used to verify the signal response of the potassium chloride. It was found that the differential refractometer detector could be used to analyze the glycerol and potassium chloride concentration. Several injections of glycerol solution followed by potassium chloride were carried out to verify the system suitability. All parameters were measured with the separate chromatograms of potassium chloride and glycerol solutions. To verify the separation properties of the resin, a synthetic solution of glycerol and potassium chloride was injected.

In order to minimize the differences due to bed dimensions of feed concentration, the effluent volume was divided by the resin bed volume and the effluent concentrations of glycerol and potassium chloride were divided by respectively the concentration of glycerol and potassium chloride in the feed solution.

The resin bed porosity was measured by injecting a very large molecule, so that molecule is not retained. By measuring the retention time of this un-retained molecule, the bed porosity is directly given in bed volumes. This parameter gives an indication of the equilibration of the resin bed packing.

EXAMPLE 2

A solution containing sodium chloride and glycerol with a glycerol concentration of 68% and a sodium level of 4.5% was injected onto the sodium form of the resin according to the procedure described in Example 1.

Parameters for the separation are summarized in the table below:

| Key technical characteristic | How is it measured and Comments |
|---|---|
| Theoretical plates for glycerol (N) N = 324 | $N = 16 \dfrac{tr^2}{\omega_0^2}$ |
| | Measured with Bed Volumes (BV) |
| Resolution (R) = Separation R = 24 (very good resolution) | $R = 2 \dfrac{(tr_{citric} - tr_{glu\cos e})}{(\omega_{citric} + \omega_{glu\cos e})}$ |
| | Measured with Bed Volumes (tr: retention time in BV, ω: peak width in BV) |
| Bed porosity (α) = 0.400 | Equal to the void volume of the resin bed |
| Overlap = Negative value | Measurement of the peak overlapping (negative value means no overlap) |

The invention claimed is:

1. A method for purification of glycerol; said method comprising steps of:
   (a) providing catalyst beads comprising gel-type acidic ion exchange resin, said beads having: (i) a uniformity coefficient no greater than 1.15; (ii) 4 wt % to 8 wt % monomer units derived from cross linker; and (iii) a harmonic mean particle size from 200 μm to 400 μm; and
   (b) allowing crude glycerol to pass through of bed of said beads.

2. The method of claim 1 in which the glycerol concentration in the crude glycerol is at least 40 wt %.

3. The method of claim 2 in which the resin has 4 wt % to 6.5 wt % monomer units derived from cross linker.

4. The method of claim 3 in which the crude glycerol passes through the bed at a flow rate of at least 0.3 bed volumes per hour.

5. The method of claim 4 in which the resin has an average particle size from 250 μm to 400 μm.

6. The method of claim 5 in which the crude glycerol is a byproduct of biodiesel production.

7. The method of claim 6 in which the crude glycerol contains a total cation concentration of at least 1 wt %.

8. The method of claim 7 in which the glycerol concentration in the crude glycerol is at least 60 wt %.

9. The method of claim 8 in which the bed is maintained at a temperature no greater than 70° C.

10. The method of claim 9 in which the resin has a uniformity coefficient no greater than 1.10.

11. The method of claim 10 in which the resin has an average particle size from 250 μm to 350 μm.

12. The method of claim 1 in which the resin has a uniformity coefficient no greater than 1.10.

13. The method of claim 12 in which the resin has an average particle size from 250 μm to 350 μm.

* * * * *